United States Patent
Hood et al.

(10) Patent No.: US 6,497,572 B2
(45) Date of Patent: Dec. 24, 2002

(54) APPARATUS FOR DENTAL TREATMENT USING HIGH PRESSURE LIQUID JET

(75) Inventors: Larry L. Hood, Laguna Hills, CA (US); Juan C. Valdes, Cota de Caza, CA (US); Steven Baldwin, San Francisco, CA (US); Randall Bailey, Dove Canyon, CA (US); Rex E. Doherty, Tustin, CA (US)

(73) Assignee: SurgiJet, Inc., Irvine, CA (US)

( * ) Notice: Subject to any disclaimer, the term of this patent is extended or adjusted under 35 U.S.C. 154(b) by 0 days.

(21) Appl. No.: 09/844,967

(22) Filed: Apr. 27, 2001

(65) Prior Publication Data

US 2001/0055742 A1 Dec. 27, 2001

Related U.S. Application Data

(63) Continuation-in-part of application No. 08/890,496, filed on Jul. 9, 1997, now Pat. No. 6,224,378.

(51) Int. Cl.[7] .................................................. A61C 5/02
(52) U.S. Cl. ........................... 433/81; 433/88; 604/140; 604/147; 606/167
(58) Field of Search ............................... 433/80, 81, 88, 433/215, 216, 82, 84, 86, 224; 601/161, 162, 165; 604/22, 140, 147; 606/167

(56) References Cited

U.S. PATENT DOCUMENTS

| | | | | |
|---|---|---|---|---|
| 3,561,433 A | * | 2/1971 | Kovach | 601/162 |
| 3,703,170 A | * | 11/1972 | Ryckman, Jr. | 601/162 |
| 5,620,414 A | * | 4/1997 | Campbell, Jr. | 604/22 |
| 6,159,006 A | * | 12/2000 | Cook et al. | 433/80 |

* cited by examiner

Primary Examiner—Cary E. O'Connor
(74) Attorney, Agent, or Firm—Harris Zimmerman, Esq.

(57) ABSTRACT

A dental instrument includes a pneumatic pressure intensifier that supplies a handpiece having an orifice to generate a high velocity liquid jet. A pneumatic system includes valves to supply the pressure intensifier and control the output to the handpiece. A jet forming assembly includes an orifice mount in the handpiece, and a guide tube assembly secured to the orifice mount. The guide tube assembly is variably positioned to select the minimum distance from the jet orifice to the tissue target, so that the jet force may be controlled.

28 Claims, 10 Drawing Sheets

APPARATUS FOR DENTAL TREATMENT USING HIGH PRESSURE LIQUID JET

REFERENCE TO RELATED APPLICATION

This application is a continuation-in-part of application Ser. No. 08/890,496, filed Jul. 9, 1997, now U.S. Pat. No. 6,224,378, issued May 1, 2001.

BACKGROUND OF THE INVENTION

The present invention relates to instruments for carrying out dental procedures, and more specifically to carrying out such procedures using a high pressure liquid jet.

It is known in the prior art and in common dental practice to carry out most treatments using mechanical techniques. For example, in endodontics, which often involves many root canal procedures, a diseased tooth is first diagnosed, and then an opening is drilled through the crown of the tooth into the pulp chamber thereof. After the tooth is isolated and the field sterilized, the pulp, consisting primarily of blood-rich tissue and nerve fiber and necrotic components, is then aspirated. There remains within the pulp chamber the primary nerve fibers and blood vessels that sustain the tooth. These tissues extend from extremely fine openings in the apex of the root(s) of the tooth through a narrow channel(s), and cannot be removed solely by aspiration.

Typically, a file is then inserted into the narrow channel(s) to displace and abrade the nerve and blood vessel tissue. Increasingly larger files are inserted, whereby the narrow channel(s) is cleared of all soft tissue. After cleaning and preparation, the pulp chamber and root channel(s) are filled with a sterile solid material, and the drilled opening is filled with standard gold, silver, or other dental filling preparations.

This typical procedure is labor-intensive, resulting in a high cost factor for the dentist's time as well as skill and experience. Moreover, the procedure may be painful, and sufficient local anesthetic must be injected to completely numb the area of the tooth for the relatively long time that the procedure requires.

Complications known to result from a root canal procedure may include infection arising from incomplete removal of the diseased tissue within the canal and pulp chamber, or the introduction of other infectious bacteria into those spaces during the procedure. In addition, the dentist may inadvertently perforate the tooth; e.g., by driving a file instrument through the apical opening at the base of the root, and the opening thus formed may provide a vector for renewed infection and inflammation. Not infrequently, drug therapy including a strong antibiotic is prescribed after the procedure to forestall these complications. Other complications include broken instruments lodged in the tooth, or fracture of the root or body of the tooth.

Recent innovations in this dental procedure include the use of laser light delivered into the pulp chamber and root channel by an optical fiber. The high power optical energy vaporizes the pulp and nerve tissue, and is inherently sterilizing. However, the products of tissue combustion may contaminate the interior of the chamber and root channel, and the laser pulses may not contact all of the tissue in the narrow root channel, causing very unsatisfactory results. To avoid these results, there is a tendency to apply an excess of laser energy, which may overheat the tooth and surrounding tissue and cause necrosis. In addition, laser energy impacting on pre-existing metallic fillings may cause dangerous reflected beams and unforeseen damage, as well as vaporized heavy metal compounds, which may be toxic.

As another example, in periodontal practice, which typically includes gingivectomy procedures, the gingiva are usually resected using a scalpel, and scaling and root planing are accomplished with specialized steel tools. These procedures and most other dental procedures are executed with mechanical drills, burrs, and cutting wheels.

Innovations such as ultrasound-driven scaling instruments, high power lasers for caries removal, and the like have not substantially altered the reliance of the dental profession on the same mechanical tools that have been in use for almost a century. All such mechanical tools generate high levels of vibration and sound that are directly conducted through bone to the ears of the patient, resulting in patient comfort problems. Also, the mechanical tools, as well as ultrasound tools, generate substantial amounts of heat in very localized areas, causing direct pain stimulation. Water spray devices are provided to remove this heat, but may not be effective at the point source of the heat. In this regard, the heat generated by dental lasers may pose the greatest problem.

Clearly the prior art shows an unmet need for improved dental instruments that can carry out a wide range of dental treatment procedures without generating heat, noise, and vibration as they operate on the patient's teeth.

SUMMARY OF THE PRESENT INVENTION

The present invention generally comprises an apparatus and methods for dental treatments that overcome the problems associated with current mechanical and dental techniques and instruments. In one aspect, the invention comprises a technique for removing the soft tissue from within a human or animal tooth, whereby infectious, inflamed and necrotic tissue may be removed and the tooth and periodontal structures restored to a healthy condition. A salient aspect of the invention is that the invention obviates the need for files and other mechanically abrasive displacement tools, employing instead a high pressure jet of water or other liquid directed at the soft tissue within the tooth to excise, emulsify and aspirate the soft tissue. The soft tissue may comprise the pulp, nerve tissue and blood vessels that extend from the surrounding jaw bone through the apex of each tooth root into the root channel and to the pulp chamber of the tooth.

The invention provides a high velocity liquid jet dental tool having a handpiece and a cannula extending therefrom. The cannula is connected to a source of high pressure water or other liquid, and includes a distal orifice to deliver a high velocity jet. The pressure range of the high pressure source is approximately 500–60,000 psi, and the jet orifice is approximately 10–800 microns in diameter. The cannula may also provide aspiration to remove the fluid and tissue from the target, or aspiration may be provided by a second cannula connected to a vacuum aspiration unit. An exemplary device is described in U.S. Pat. No. 5,562,692.

To initiate a treatment method of the invention, a tooth that is diagnosed as diseased and in need of a pulpectomy/root canal procedure is opened; that is, a hole is made in the crown of the tooth using a standard dental grinding or drilling instrument. The tooth is then isolated using a dental dam or similar protective shield.

The cannula of the high velocity liquid jet tool is then directed through the newly formed hole in the crown of the tooth, and a jet of liquid is directed at the pulp and nerve and vascular tissue within the interior chamber of the tooth. The fluid may comprise medical-grade saline solution, and/or a disinfectant solution and/or an antibiotic solution and/or an abrasive solution. In the pressure range and jet diameter formed by the high velocity liquid jet tool, all the soft tissue within the tooth is cut, excised, emulsified, and aspirated out of the tooth. Aspiration may be provided by the high velocity liquid jet tool, or by the cannula of a standard dental aspiration device.

A salient aspect of the method of the invention is that the high velocity liquid jet easily removes all the soft tissue within the tooth, but is limited in its ability to cut or erode the hard calcified tooth tissue. Likewise, the jet lacks the velocity to cut through the apical root openings through which the nerve fibers and blood vessels enter the root channels from the surrounding jaw tissue. As a result, this process of pulpectomy/root canal progresses to a self-limiting extent and for example, cannot pierce the apical openings if they are naturally closed, whereby a source or complications known to result from prior art procedures. In addition, the use of antiseptic or antibiotic solutions reduce the possibility of post-procedure infection if the apical openings where to be damaged.

Moreover, the time required to excise, emulsify, and aspirate all the soft tissue within a typical molar is on the order of 10–240 seconds, so that far less time and labor is expended in the procedure. This reduction in time to complete the removal step reduces the need for local anesthesia, reduces the time that the patient may experience pain (if any), and overall increases throughput in a dental practice.

The interior chamber of the tooth is then completely aspirated and verified for completion of removal of all soft tissue. The interior chamber is then packed with an appropriate filler material known in the prior art, and the opening in the top of the tooth is filled or provided with a prosthetic crown, as is known in the dental art.

It should be noted that the fluid jet may comprise a pulsed jet formed by a pulse intensifier device in the handpiece of the dental high velocity liquid jet tool, as described in the US patent to Bair referenced above. Alternatively, the handpiece may be connected to a source of high pressure fluid to form a steady stream jet emanating from the orifice. The handpiece may be directed at other surfaces and structures to carry out endodontal, periodontic, surgical, and restorative procedures such as gingivectomy, removal of granulation tissue, muco-osseous surgery, caries removal, scaling and removal of plaque and calculus, and extractions and tissue incisions.

DESCRIPTION OF THE PREFERRED EMBODIMENT

The present invention generally comprises an apparatus and methods for dental treatments that overcome the problems associated with current mechanical and dental techniques and instruments. In one aspect, the invention comprises a technique for carrying out a pulpectomy or root canal: that is, removing the soft tissue within the tooth by excising, emulsifying and aspirating the soft tissue.

Figure 1:
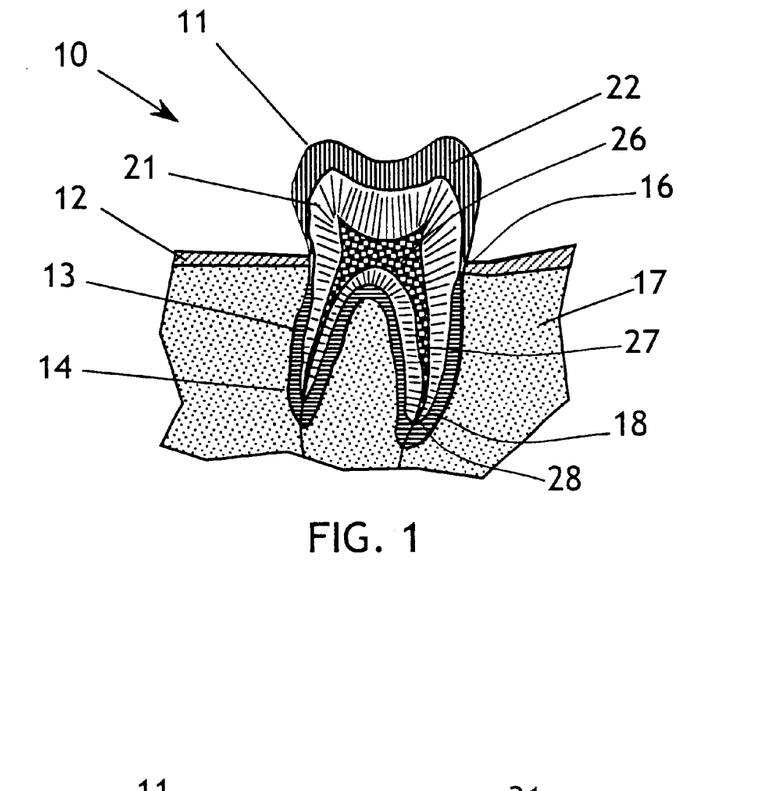
FIG. 1 is a cross-sectional elevation of a typical human tooth prior to undergoing the pulpectomy/root canal procedure of the present invention.

With regard to FIG. 1, a typical human tooth 10 is comprised of a crown 11 extending above the gum tissue 12, at least one root portion 13 received within a respective alveolus 14, and a neck portion 16 joining the root and crown at the cemento-enamel junction. The alveoli are deep depressions in the bone tissue of the mandible 17, and are lined with periosteum which is reflected on the tooth at the apex 18 of each root. At the margin of the alveolus the periosteum becomes continuous with the periodontal ligament of the gum tissue 12. The hard tissue of the tooth includes the dentine 21, which provides the primary structure of the tooth, and the very hard enamel layer 22 which forms a durable grinding surface and covers the crown 11 down to the cemento-enamel junction at the neck 16.

Within the dentine layer 21 there is defined a pulp chamber 26. Processes of the pulp chamber 26, termed the root canal 27, are disposed centrally in each root 13 and extend through the respective apex 18 at a minute orifice, the apical foramen 28. The chamber 26 and canal(s) 27 contain dental pulp, a soft, vascular tissue containing numerous nerves and blood vessels and other tissue components. The pulp provides enervation and sustenance to the tooth through the epithelial lining of the pulp chamber and canals.

Figure 2:
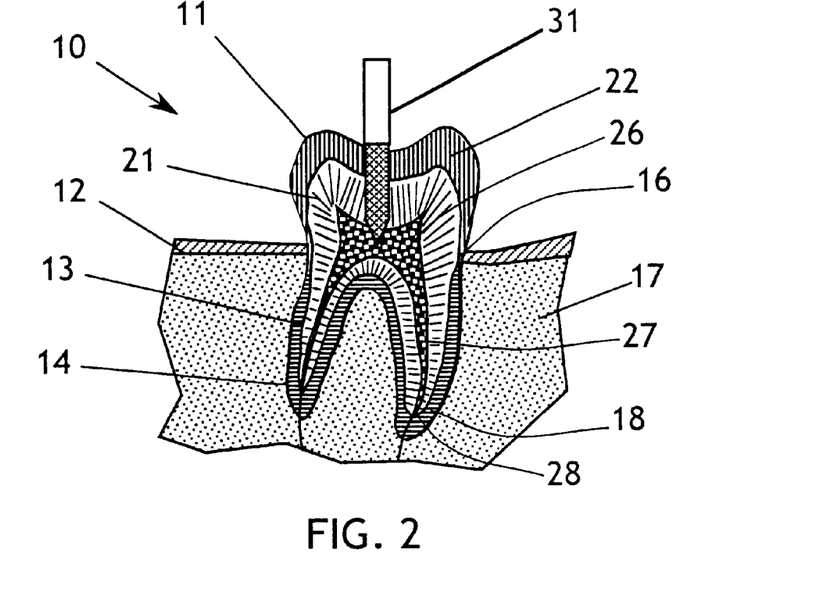
FIG. 2 is a cross-sectional elevation as in FIG. 1, showing the step of creating an opening through the top of the tooth to the pulp chamber within.
Figure 3:
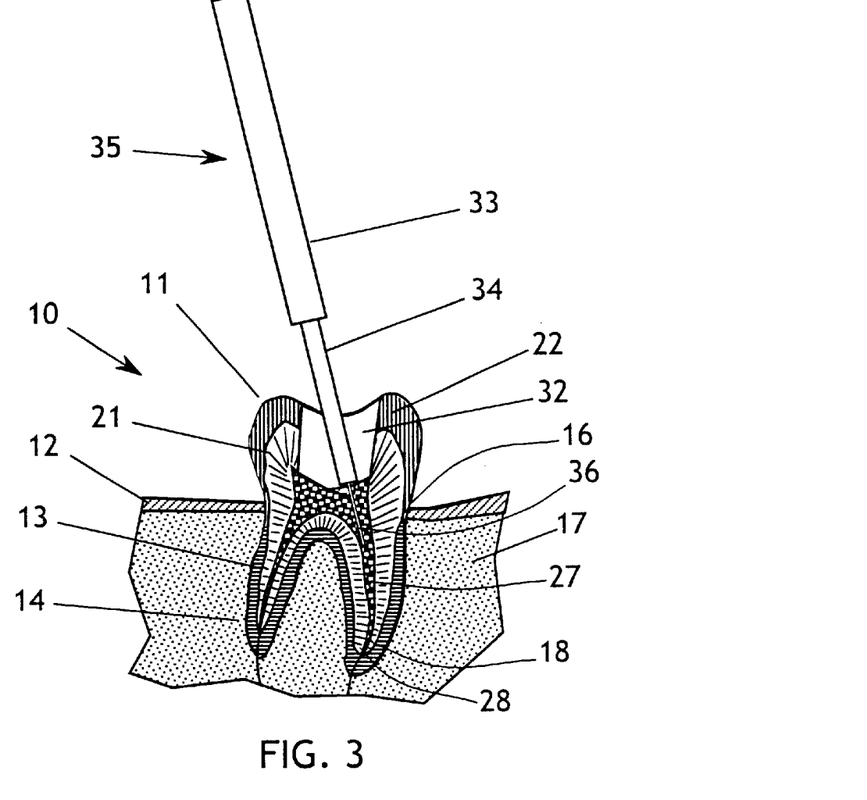
FIG. 3 is a cross-sectional elevation as in FIGS. 1 and 2, showing the cannula of the dental high velocity liquid jet tool being extended through the upper opening of the tooth and being actuated to emit a high pressure, high velocity jet.

The method of the present invention is used to treat a tooth that is diagnosed as diseased and requiring a pulpectomy/root canal procedure. With regard to FIG. 2, the tooth is initially opened by employing a dental drill 31 or equivalent burr or grinding tool. The resulting opening 32 extends through the enamel and dentine to provide access to the pulp chamber 26 and root channels 27, as shown in FIG.

3. A high velocity liquid jet dental tool 35 is provided, including a handpiece 33 having a cannula 34 extending therefrom. The cannula includes a distal orifice adapted to generate a high velocity, high pressure, low volume jet 36 of liquid. The handpiece maneuvered to insert the cannula 34 into the opening 32 to direct the jet 36 at the soft tissue within the chamber 26 and channels 27. The jet easily cuts through the soft tissue, and the energy and turbulence engendered by the jet causes the tissue to be emulsified upon contact. Moreover, the turbulent liquid easily penetrates into the narrow spaces of the root channels 27 (FIG. 4), effecting thorough excision and emulsification of the nerve and vascular tissue therein. The cannula 34 may also provide vacuum aspiration to remove the emulsified tissue and jet fluid, or a second aspiration cannula may be employed.

Figure 4:
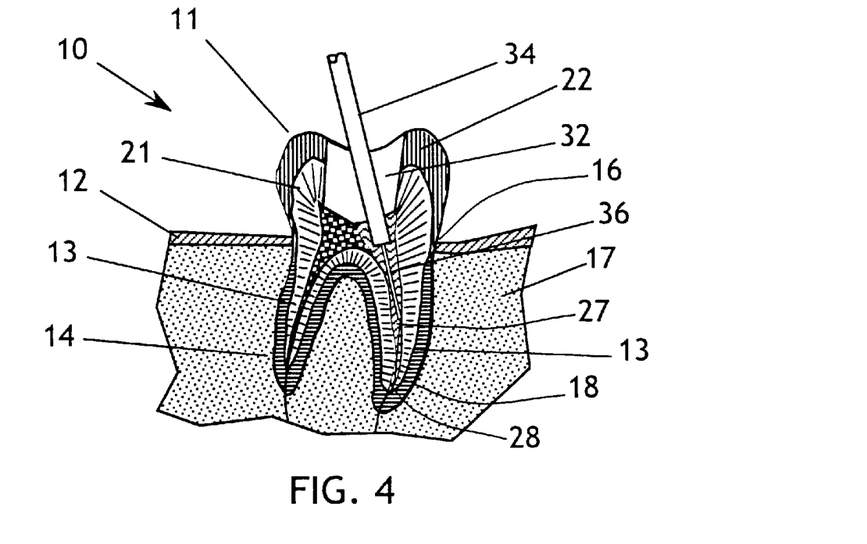
FIG. 4 is a cross-sectional elevation as in FIGS. 1–3, showing the soft tissue within one root channel and a portion of the pulp chamber emulsified and undergoing aspiration.

In the preferred embodiment the pressure range of the high pressure jet is approximately 500–60,000 psi, and the jet diameter is approximately 10–800 microns. These parameters are selected to provide a liquid jet that is not capable of cutting nor detrimentally eroding the hard tissue of the tooth. As a result, the excision and emulsification action of the jet 36 cannot pass through the apical foramen 28 of the root, if the foramen is naturally closed, and thus cannot injure the alveolar sac or periosteum at the base of the root. Thus a source of substantial post-operative complications in prior art procedures is completely eliminated by the self-limiting feature of the invention.

Figure 5:
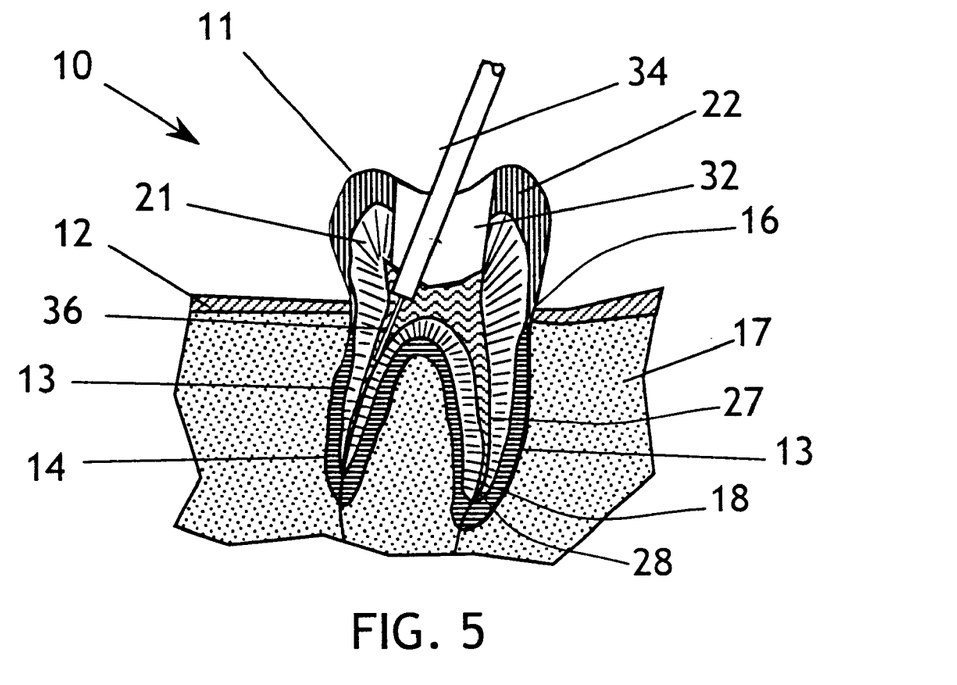
FIG. 5 is a cross-sectional elevation as in FIGS. 1–4, showing the soft tissue within both root channels and all the pulp chamber emulsified and undergoing aspiration.

The jet 36 acts quickly within the soft tissue, and the time necessary to excise, emulsify, and aspirate all the soft tissue within a typical tooth is approximately 10–240 seconds. Of course, more time is required for teeth such as molars having a plurality of root channels 27. As shown in FIG. 5, the dental high velocity liquid jet tool 35 may be maneuvered to direct the cannula 34 and jet 36 into each of the root channels to remove all soft tissue therein.

The liquid which constitutes the jet 36 may comprise sterile water or medical grade saline solution, or an antiseptic solution, or an antibiotic solution, or an abrasive solution, or other medications or chemicals, or any combination thereof. Furthermore, more than one of these types of solutions may be used in serial order. For example, saline solution may be used for the excision and emulsification process, followed by an abrasive solution to scour the cavity, an antiseptic solution to eliminate indigenous bacteria and then an antibiotic solution to prevent regrowth of infective agents. It should be noted that the fluid jet may comprise a pulsed jet formed by a pulse intensifier device in the handpiece of the dental high velocity liquid jet tool, as described in the US patent to Bair referenced above. Alternatively, the handpiece may be connected to a source of high pressure fluid to form a steady stream jet emanating from the orifice.

Figure 6:
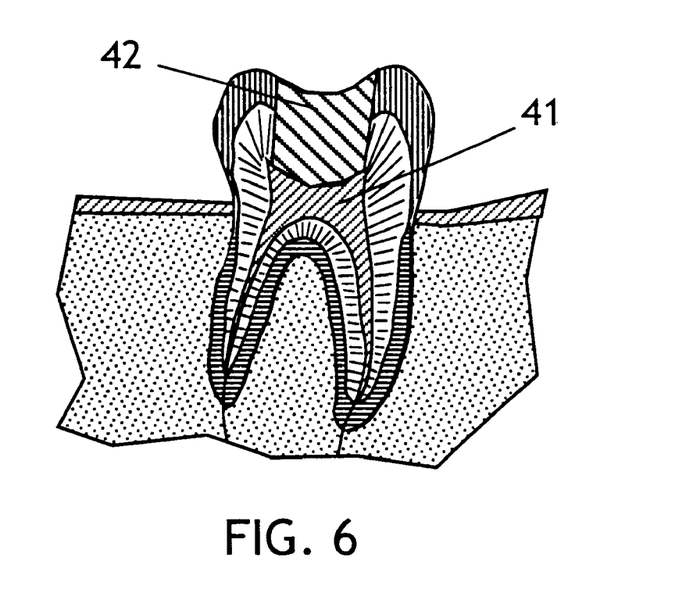
FIG. 6 is a cross-sectional elevation as in FIGS. 1–5, showing the pulp chamber and root channels packed with filler material and the upper opening filled at the completion of the procedure.

After the pulp chamber and root channels have been fully aspirated and visualized for verification of removal, the pulp chamber and root channels are packed with an inert, aseptic material 41, as is known in the dental art. Thereafter, the opening 32 is filled using a standard dental material 42, such as silver amalgam, gold inlay or crown, cured composite material, or the like. The procedure is thus completed.

The use of the high velocity liquid jet to perform the pulpectomy/root canal procedure exhibits the following advantages over prior art techniques:

1) Complete removal of all soft tissue within the pulp chamber and root channels;

2) Rapid completion, resulting in reduced use of anesthetic and reduced pain experienced by patient, and reduced cost of skilled dentist and office overhead expenses;

3) Elimination of complications due to perforation of root or apical foramen;

4) Sterilization of operating field by use of appropriate jet liquids to minimize post-operative infection.

A preferred embodiment of the apparatus for carryout out the procedure described above may include a pneumatic/hydraulic apparatus. (Note that the pressure values stated herein are exemplary only, and may be selectively varied in accordance with standard mechanical design principles.) With regard to FIG. 7, the pneumatic portion 51 of the apparatus includes an input connector 52 that is coupled to a pressurized air or gas source, such as a standard 150 psi supply typically available in a dental service installation. The input feed is limited by a 175 psi pressure relief valve 53, and feeds a supply line 59. Connected to the supply line 59 is a mechanical pressure regulator 54 that is coupled to gauge 57 that may be visualized by the operator. The regulator feeds 50 psi pneumatic pressure to a pair of solenoid valves 58A and 58B. The valves 58 feed operating pressure to respective ON and OFF sides of a three way hydraulic valve 81 in the hydraulic section of the apparatus, describe below and shown in FIG. 8. A 120 psi pressure switch 56 is connected to the supply line to assure sufficient pressure to operate the pneumatic system.

Figure 7:
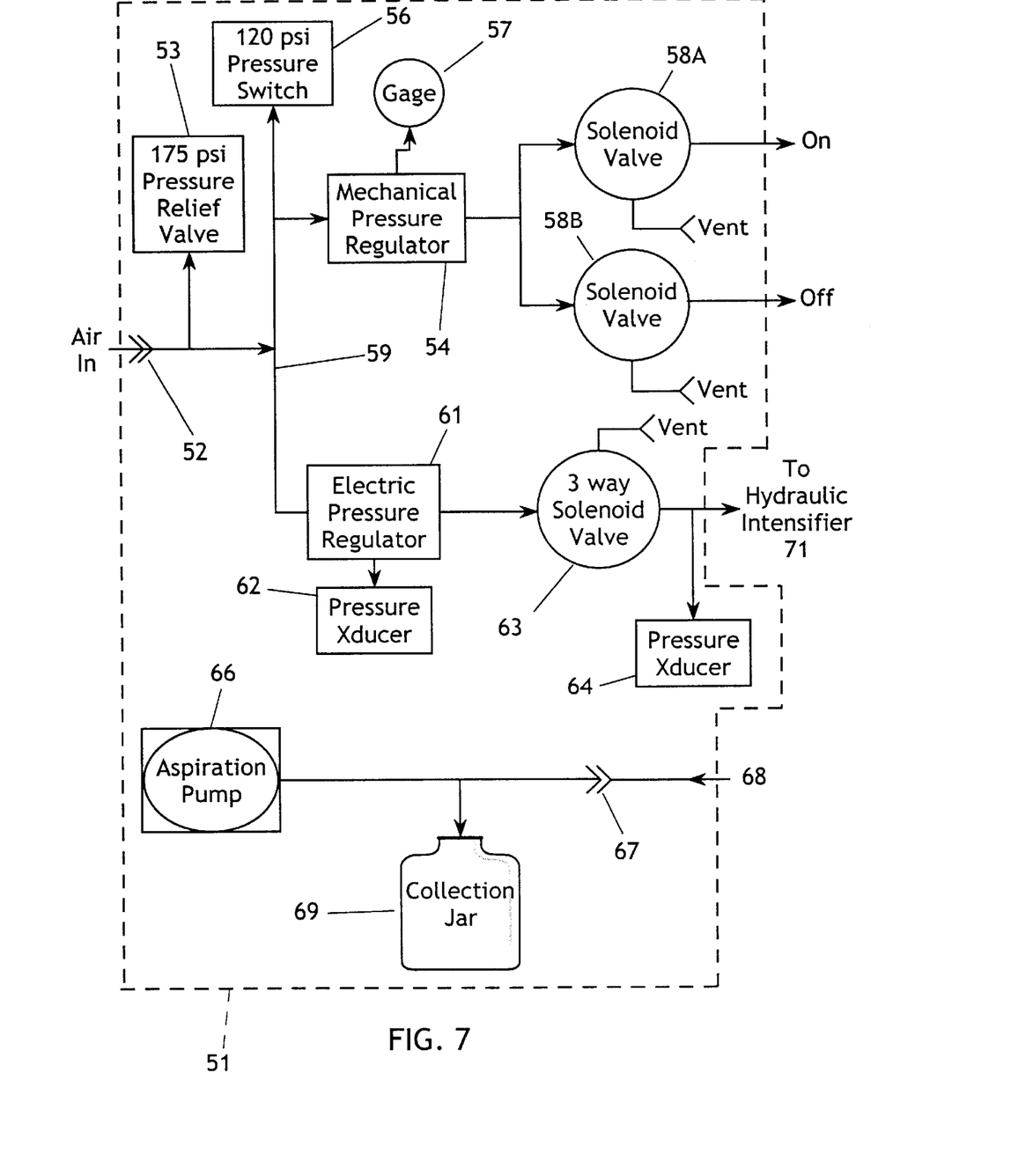
FIG. 7 is a schematic view of the pneumatic system of the present invention.
Figure 12:
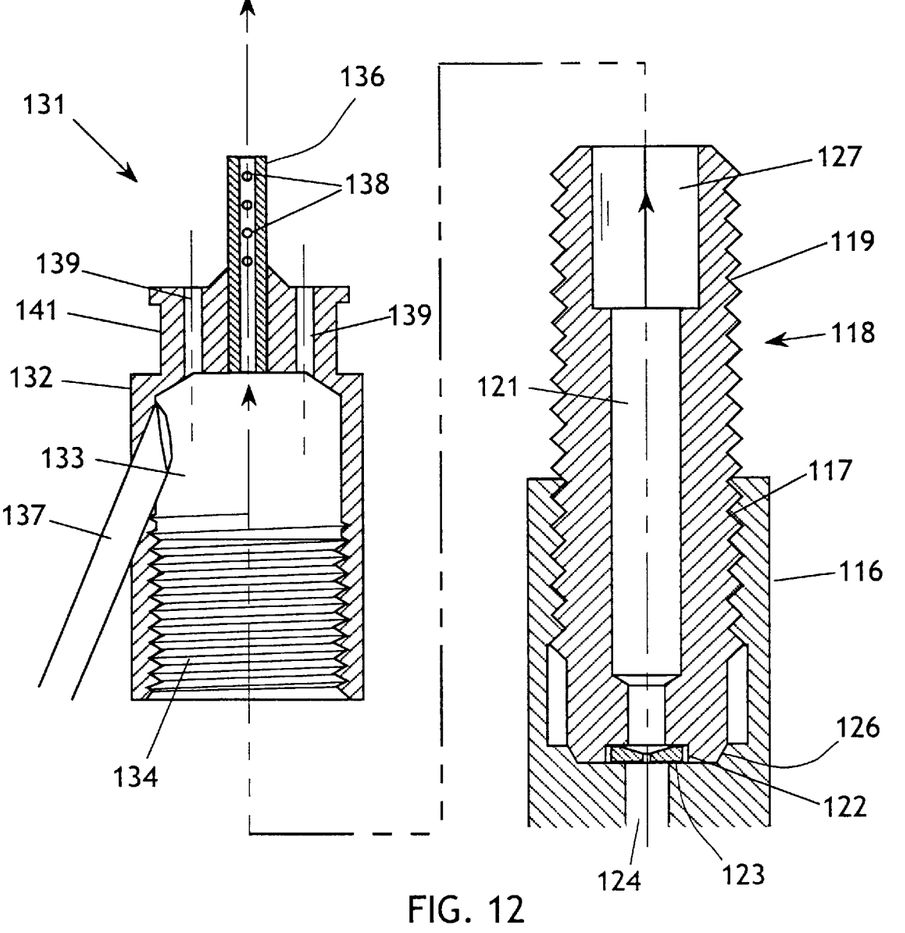
FIG. 12 is an exploded view showing the orifice mount and guide tube assembly of the invention.

The supply line 59 also feeds an electric pressure regulator 61, which may have an adjustable range of 0–70 psi. which is monitored by a pressure transducer 62. The regulator 61 feeds a three way solenoid valve 63, one output of which is fed to a pressure transducer 64 and hydraulic intensifier 71 (shown in FIG. 8 and described below), the other output being vented to atmosphere. The pneumatic system also includes an aspiration pump 66 which is coupled through a quick connect 67 to an aspiration hose 68 and thence to the operator's handpiece through tubing 137, as shown in FIG. 12. A collection jar 69 is connected between the quick connect and the pump 66 to capture aspirant (liquid, blood, tissue debris, etc.) from the operator's handpiece, as also detailed in the following description.

Figure 8:
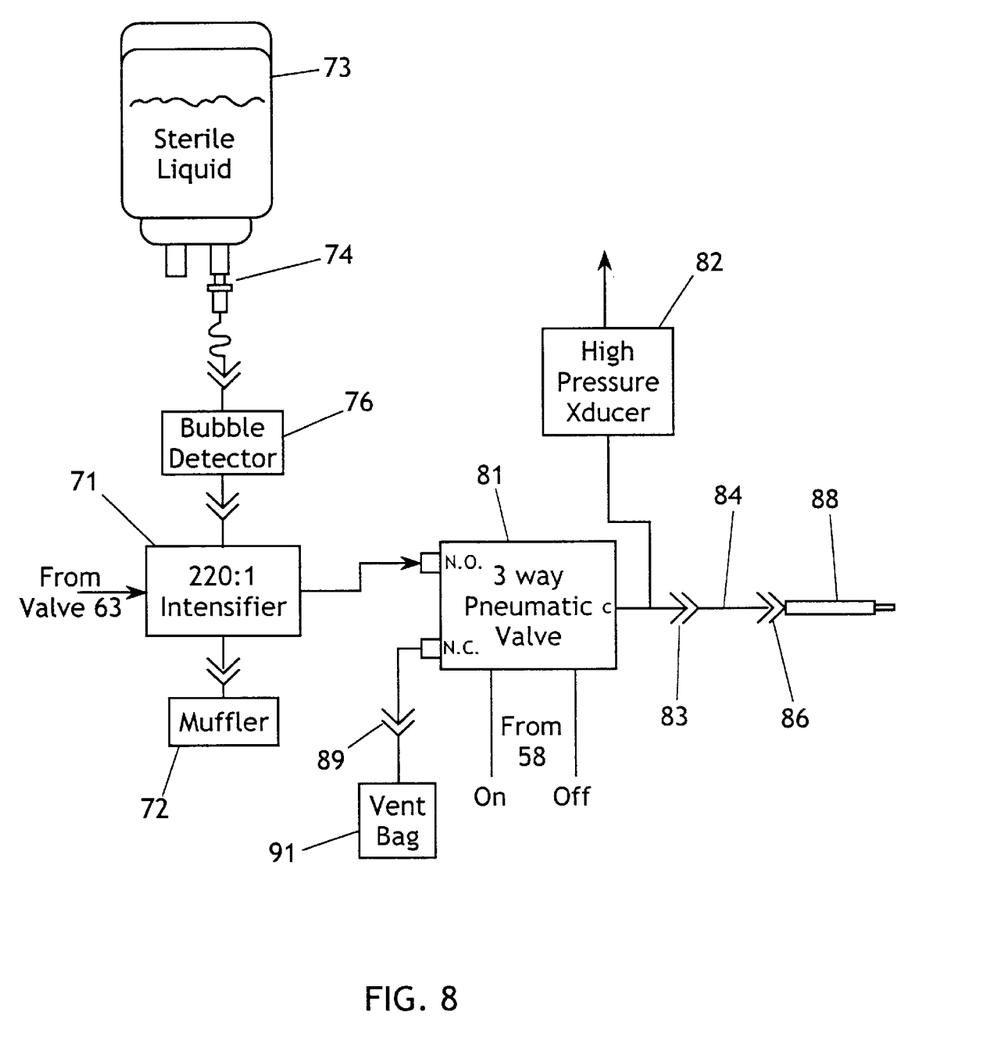
FIG. 8 is a schematic view of the hydraulic system of the present invention.

With regard to FIG. 8, the hydraulic system of the invention includes a pressure intensifier 71 that receives pneumatic operating pressure from valve 63 and exhausts into muffler 72. The intensifier 71 is connected to a liquid supply comprising a liquid reservoir such as a bag 73 of sterile water or the like that may be mixed with agents such as antibiotics, abrasives, antiseptics, and the like. The bag 73 is connected to a standard irrigation connector 74 similar to an IV setup, and fed to a bubble detector 76 that halts operation of the system when flow is interrupted or the bag 73 is emptied.

The output of intensifier 71, which is a high pressure, sterile liquid stream, is fed to the normally open port of a three way pneumatic valve 81. The valve 81 is driven to open and close by pneumatic inputs from valves 58, so that the relatively low pressure air supply may be used for on/off control of the relatively high pressure output of the intensifier 71. The high pressure output of the valve 81 is monitored by a high pressure transducer 82 and connected through a high pressure quick connect 83 to a high pressure supply hose 84. A quick connect 86 joins the hose 84 to the operator's handpiece 88. The normally closed output of the valve 81 is coupled through quick connect 89 to a vent bag 91.

It is noted that the outputs of the transducers 62 and 64, pressure switch 56, transducer 82, and bubble detector 76 are all connected to a microprocessor (not shown) which is programmed to accept these inputs and control the performance of the combined systems and assure safe operation.

Figure 9:
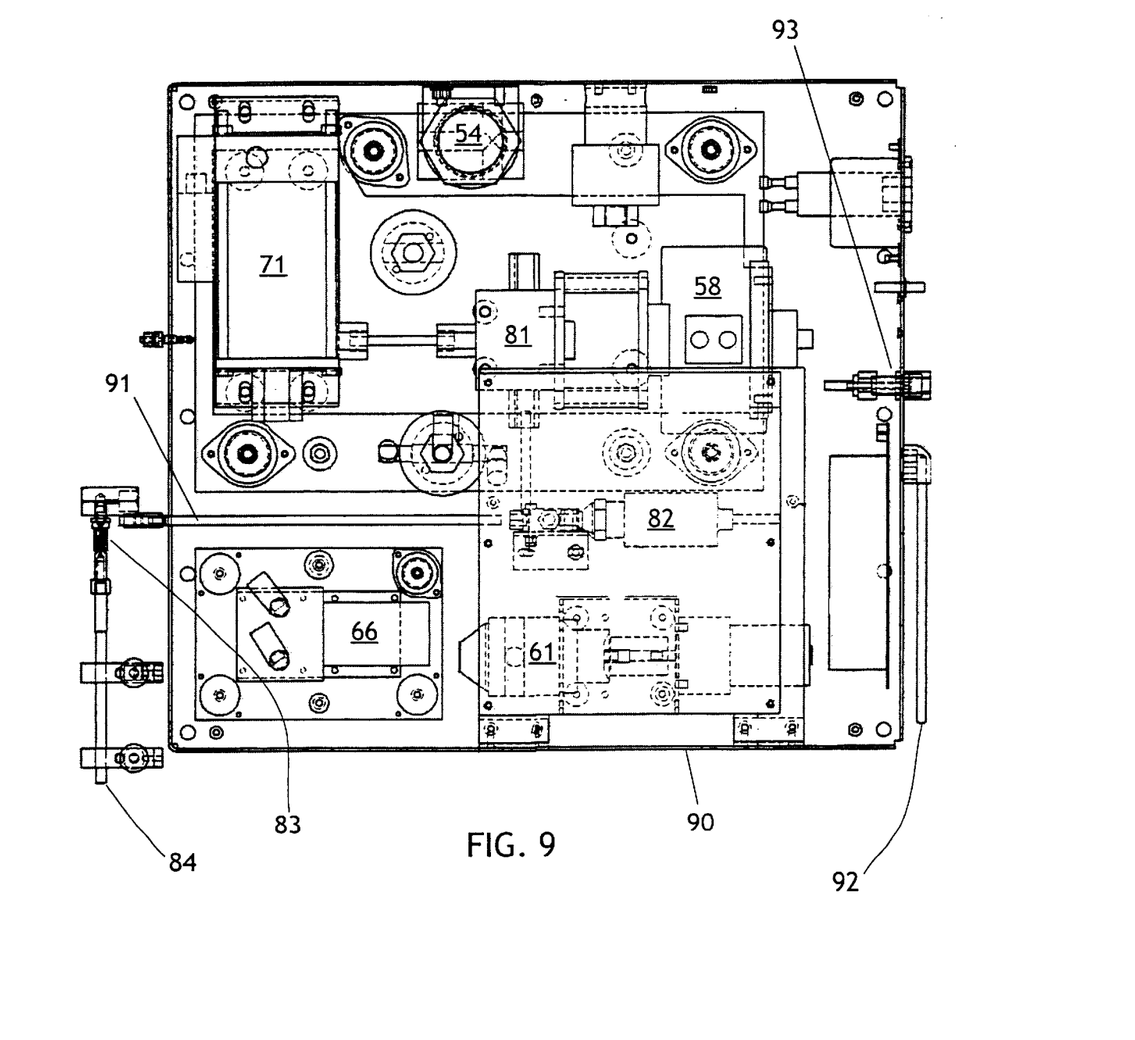
FIG. 9 is a plan view of a mechanical layout embodying the pneumatic and hydraulic systems of FIGS. 7 and 8.

With regard to FIG. 9, there is shown a mechanical layout in which the major components are labeled with reference numerals ascribed above. The entire system may be embodied in a housing 90 that is sufficiently small (i.e., approximately 20 inches square) to be used in a typical dental service installation, or to be used as a portable instrument to service multiple dental treatment rooms. The high pressure liquid output is conducted through pipe 91 to quick connect 83, and thence through high pressure hose 84 to the handpiece 88. A hook 92 extends from the housing to support the vent bag 91. A control input connector 93 permits the system to be controlled by a foot switch, such foot switch arrangements being common in the dental arts.

To summarize the operation of the pneumatic/hydraulic systems of the invention, a bag 73 is first connected through bubble detector 76 to the pressure intensifier 71, and the apparatus is connected to electrical power and a pneumatic air supply. The aspiration pump 66 is switched on to provide sufficient suction to clear the dental operation site of liquid and tissue debris. A handpiece is connected by quick connect 86 through high pressure tube 84 to the output of the valve 81. Thereafter, the foot switch is used by the operator to actuate solenoid valves 58A and 63, thereby directing air pressure to the hydraulic intensifier 71 and to open the valve 81. Thus high pressure liquid is pumped to the handpiece 88, where it is directed as a high velocity jet to carry out dental procedures such as root canal procedures and other soft tissue operations. When the foot switch is released, the solenoid valve 58A opens and 58B closes, switching the valve 81 to block flow to the handpiece and to shunt any residual pressure to the vent bag 91. At the same time, the solenoid valve 63 switches to block pneumatic operating pressure to the intensifier 71. Thus the high velocity jet ceases immediately.

Figures 10, 11:
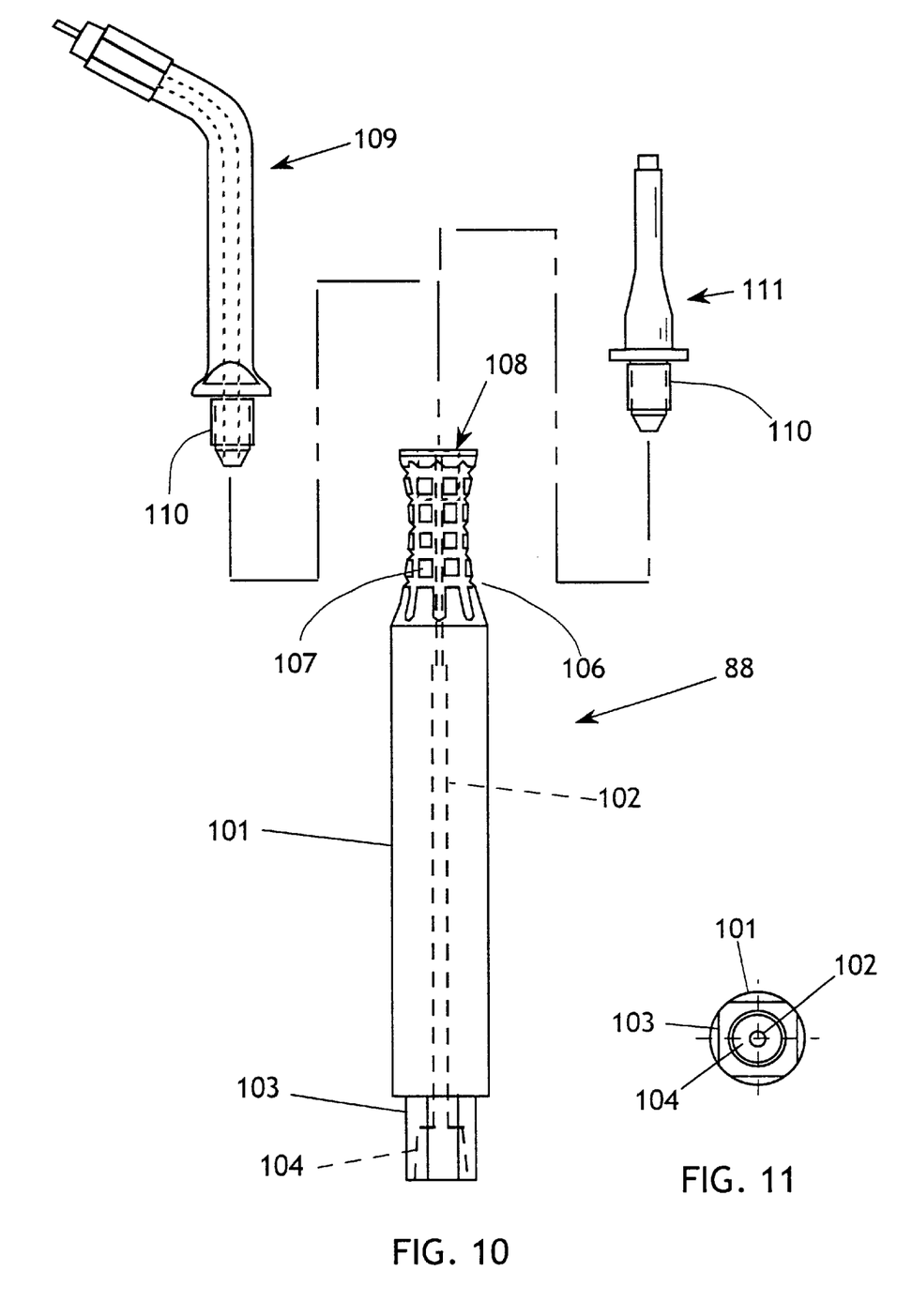
FIG. 10 is an exploded view showing a handpiece and two interchangeable tip assemblies of the present invention.
FIG. 11 is an end view showing the quick connect coupling of the handpiece of the invention.

With regard to FIGS. 10 and 11, one embodiment of the handpiece 88 includes a tubular barrel 101 having a central passage 102 extending axially therethrough. The proximal end of the barrel 101 terminates in a rectangular projection 103 that is adapted to engage a quick connect fitting 86. A recess 104 extending axially into the projection 103 is adapted to receive a ultra-fine filter assembled to the quick connect fitting. At the distal end of the barrel 101, a concave annular portion 106 is provided with a high friction surface 107 to enhance grasping by the opposed finger and thumb of the user. A receptacle 108 is formed in the distal end of the barrel 101 to receive a complementarily formed end 110 of interchangeable jet tube assemblies. For example,jet tube assembly 109 includes an angled distal end, and jet tube assembly 111 comprises a shorter, linear tubular shape. The ends 110 are machined to form a 20 Kpsi metal-to-metal seal with the receptacle 108, and to be secured therein by frictional engagement that is manually releasable.

The distal end of each jet tube assembly includes a jet forming arrangement. With regard to FIGS. 12–17, the distal end 116 of a jet tube assembly is provided with a threaded socket 117 adapted to receive an orifice mount 118. The mount 118 is formed similarly to an elongated set screw, with fine external threads 119 to engage the socket 117 and a stepped flow passage 121 extending axially therethrough. At the proximal end of the mount 118, an annular recess 122 is formed to secure a disc-like orifice jewel 123, which has a central orifice therethrough having a diameter in the range of 20–100 microns. The passage 124 of the jet tube assembly supplies very high pressure liquid to the base of the orifice jewel, and a high velocity jet emanates from the orifice as a highly collimated beam that travels distally through the passage 121 along the axis thereof. A beveled proximal surface 126 of the orifice mount-is machined to high tolerances and polished to form an intimate seal with the inner end of the socket 117 and form a high pressure seal therewith. The distal end of the orifice mount is provided with a socket 127 adapted to receive a hex key to facilitate installation and adjustment.

Figure 13:
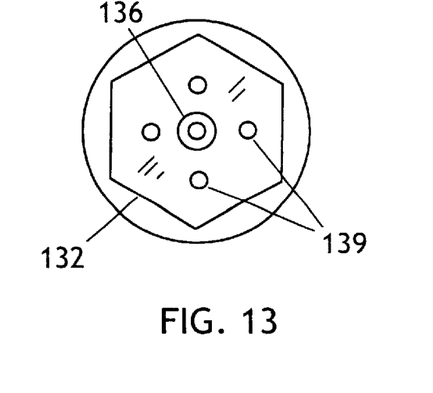
FIG. 13 is an end view of the guide tube assembly shown in FIG. 12.
Figure 14:
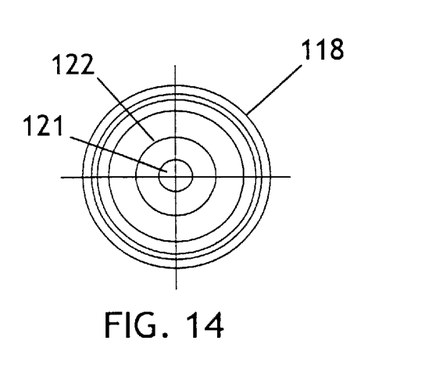
FIG. 14 is a proximal end view of the orifice mount shown in FIG. 12.
Figure 15:
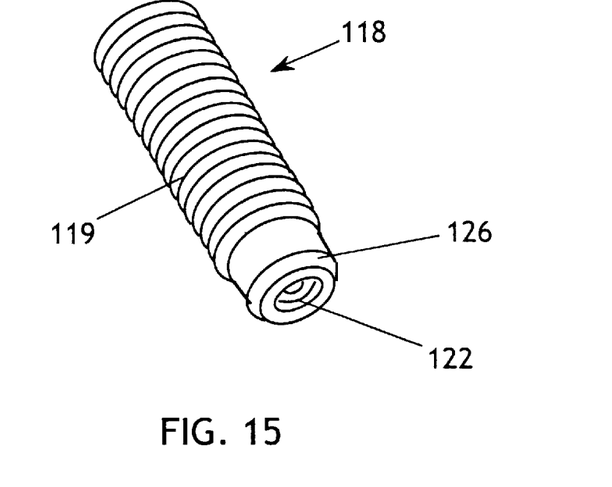
FIG. 15 is a perspective view of the orifice mount shown in FIG. 12.

As also shown in FIGS. 12 and 13, a guide tube assembly 131 includes a housing 132 having an hexagonal outer conformation to permit engagement by a standard tool or wrench. The tubular interior cavity 133 is threaded (134) from the proximal end to the medial portion thereof and adapted to engage the threads 119 of the orifice mount 118. A guide tube 136 extends distally and axially from the housing 132, and provides a shielded pathway for the high velocity jet emanating from the jewel orifice 123. An aspiration tube 137 is coupled to the cavity 133 to apply suction thereto. A plurality of aspiration ports 138 are provided in the guide tube 136 to apply suction and aspirate flowable materials from the site of the operation (the tissue target of the high velocity jet). In addition, further aspiration ports 139 are formed in the distal end of the housing 132 to provide widespread aspiration that collects widespread sprayed material, and to prevent vacuum buildup if the ports 138 become blocked. Note that the guide tube configuration may vary in size, length, and diameter to accommodate various size teeth, different procedures, and other circumstances. All have one ore more aspiration ports to reduce liquid jet backup pressure and remove fluid build up.

It is significant to note that the housing 132 may be adjustably positioned on the orifice mount, whereby the distance from the orifice jewel to the tissue target may be selected, with the housing 132 and the guide tube 136 acting as a standoff. Due to the fact that the jet beam force decreases with the square of the distance traveled from the orifice, the selective positioning of the housing 132 enables the user to control the impact force of the jet beam and thus control the effect on tissue.

Figure 16:
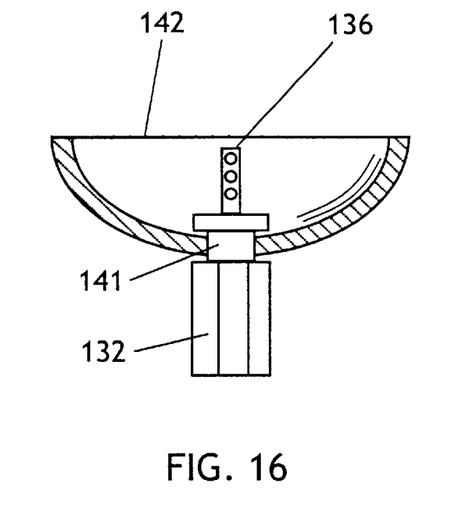
FIG. 16 is a side view showing the jet shroud assembled to the guide tube assembly of the invention.
Figure 17:
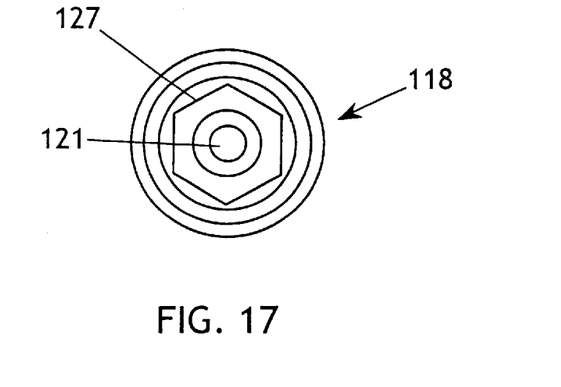
FIG. 17 is a distal end view of the orifice mount shown in FIG. 12.

With regard to FIG. 16, a smooth cylindrical neck portion 141 of the housing 132 is provided to support a shroud 142. The shroud 142 comprises a curved concave member having a central opening that is received about the neck 141, the shroud extending about the guide tube 136 to confine spray from the impact site of the jet. The shroud may be formed of transparent plastic or polymer material to permit visualization of the operation site. Note that the aspiration ports 138 and 139 are all functioning within the confines of the shroud to remove aspirant as it is confined and collected.

Figure 18:
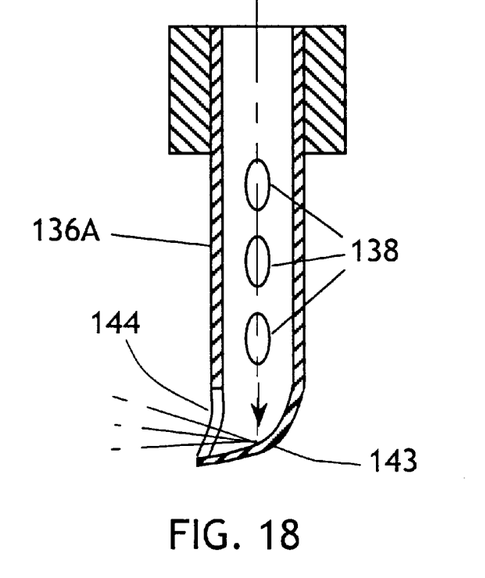
FIGS. 18–20 are cross-sectional side views of further embodiments of the guide tube of the invention.

With reference to FIG. 18, a variant of the guide tube 136A includes a distal end 143 that is closed, curved, and angled obliquely. An outlet port 144 is placed in the side wall of the guide tube. The high velocity coherent jet beam impacts on the end wall 143 and forms a high velocity spray, which is directed through the port 144. The high velocity spray is useful for procedures other than cutting and emulsification, such as superficial cleaning and the like.

Figure 19:
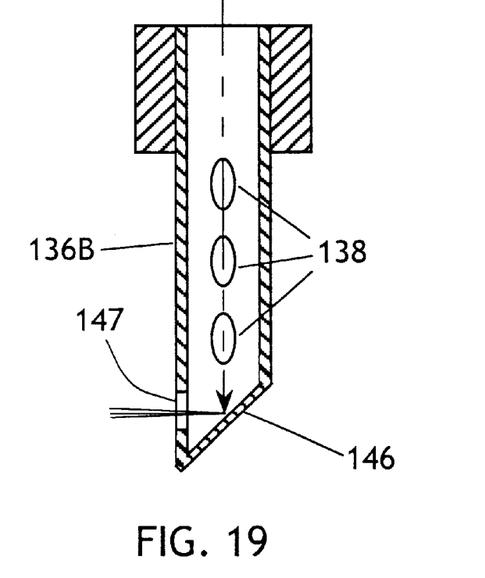

Likewise, with reference of FIG. 19, a variant of the guide tube 136B includes a distal end 146 that is closed, planar, and angled obliquely. An outlet port 147 is placed in the side wall of the guide tube. The high velocity coherent jet beam impacts on the end wall 146 and forms a high velocity spray, which is directed through the port 147. In either of the embodiments of FIGS. 18 and 19, the guide tube may be rotatably mounted in the housing 132 to permit the port 144 or 147 to be directed at any angle about the axis of the assembly, thereby providing greater utility in the narrow confines of oral operations.

Figure 20:
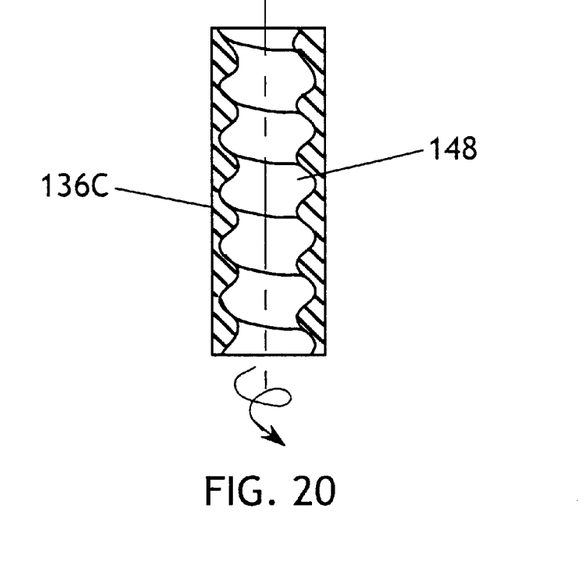

With regard to FIG. 20, a variant of the guide tube 136C includes a distal opening aligned with the axis of the tube, and the interior bore of the tube is provided with a helical surface, similar to a rifling surface, that influences the passing jet beam to impart a turbulent, swirling effect thereto. This effect broadens the impact zone of the jet and reduces the cutting action, while augmenting other aspects of the jet effect, such as abrasion and emulsification.

It may be appreciated that the high velocity liquid jet dental instrument disclosed herein may be employed to carry out other treatments and procedures in addition to root canal and pulpectomy. For example, the fluid jet is exceptionally well suited to carry out removal of calculus and plaque, and for root planing. This process may be enhanced through the use of an abrasive solution as the fluid for the fluid jet. Likewise, the fluid jet may be used for excision and resection of the gingiva, removal of granulated tissue, as well as muco-osseous surgery. The fluid jet may also be an adjunct to tooth extraction, in that the jet ay be used to sever the fibrous attachments to the tooth root, thereby easing the subsequent extraction. These procedures may be aided by the use of antibiotic solutions to form the fluid jet.

Furthermore, a fluid jet of sufficient energy may be used to remove various dental tissue, thereby providing simple caries removal and preparation for filling. It has been found that proper choice of jet energy selectively removes the various tissue while the health surrounding enamel and dentine may remain unscathed by the jet. This process may be enhanced through the use of an abrasive solution as the fluid for the fluid jet.

The high velocity liquid jet dental instrument provides all of these treatment options, as well as the root canal/pulpectomy procedure, while creating virtually no heat or vibration at the target site. This characteristic is a notable advance over prior art mechanical tools, ultrasound instruments, and dental lasers.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiments described are selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

What is claimed is:

1. A high velocity liquid jet dental instrument, including:
   reservoir means for supplying liquid to said jet;
   pneumatic pressure intensifier means for receiving liquid from said reservoir means and generating a high pressure liquid output;
   a dental handpiece;
   first valve means for controlling the flow of said high pressure liquid output to said handpiece;
   jet orifice means in said handpiece for receiving said high pressure liquid output and forming a high velocity, narrow jet beam.

2. The high velocity liquid jet dental instrument of claim 1, further including a pneumatic pressure source connected to power said pneumatic pressure intensifier means.

3. The high velocity liquid jet dental instrument of claim 2, wherein said first valve means includes a first pneumatic valve interposed between said pressure intensifier and said handpiece.

4. The high velocity liquid jet dental instrument of claim 3, wherein said first pneumatic valve comprises a three way valve that may be switched on to pass said high pressure liquid output to said handpiece, and switched off to vent pressure from said handpiece.

5. The high velocity liquid jet dental instrument of claim 4, further including first solenoid valve means for controlling said first pneumatic valve, said first solenoid valve means being controlled by an operator switch.

6. The high velocity liquid jet dental instrument of claim 5, further including second pneumatic valve means for controlling the pneumatic supply to said pressure intensifier.

7. The high velocity liquid jet dental instrument of claim 6, further including second solenoid valve means for controlling said second pneumatic valve means, said second solenoid valve means being controlled by said operator switch.

8. The high velocity liquid jet dental instrument of claim 1, wherein said handpiece includes a generally tubular barrel, and at least one jet tube assembly removably secured to said tubular barrel.

9. The high velocity liquid jet dental instrument of claim 8, wherein said jet tube assembly includes a distal end, and an orifice mount received in a socket formed in said distal end of said jet tube assembly.

10. The high velocity liquid jet dental instrument of claim 9, wherein said socket is threaded internally, and said orifice mount includes external threads having a portion adapted to engage said internal threads of said socket.

11. The high velocity liquid jet dental instrument of claim 9, wherein said orifice mount includes a bore extending axially therethrough, and an orifice jewel secured in a recess in a proximal end of said orifice mount.

12. The high velocity liquid jet dental instrument of claim 11, wherein said orifice jewel includes an ultra-fine orifice for receiving said high pressure liquid output and forming a high velocity liquid jet beam directed distally through said bore.

13. The high velocity liquid jet dental instrument of claim 12, further including a guide tube assembly secured to said orifice mount.

14. The high velocity liquid jet dental instrument of claim 13, wherein said guide tube assembly includes a tubular internal cavity having internal threads adapted to engage said external threads of said orifice mount.

15. The high velocity liquid jet dental instrument of claim 14, said guide tube assembly further including a guide-tube extending distally and axially and aligned to provide a shielded pathway for said jet beam emanating distally from said orifice.

16. The high velocity liquid jet dental instrument of claim 15, further including means for connected aspiration suction to said tubular internal cavity of said guide tube assembly.

17. The high velocity liquid jet dental instrument of claim 16, further including at least one aspiration port extending transversely through said guide tube.

18. The high velocity liquid jet dental instrument of claim 16, further including a distal end wall of said guide tube assembly through which said guide tube extends distally.

19. The high velocity liquid jet dental instrument of claim 18, further including at least one aspiration port extending through said distal end wall of said guide tube assembly.

20. The high velocity liquid jet dental instrument of claim 16, further including a spray shroud joined to said guide tube assembly.

21. The high velocity liquid jet dental instrument of claim 20, wherein said shroud includes a concave member secured about the distal end of said guide tube assembly and connected to said aspiration suction.

22. The high velocity liquid jet dental instrument of claim 21, wherein said shroud is formed of transparent material to permit visualization of the jet target impact site.

23. The high velocity liquid jet dental instrument of claim 15, wherein said guide tube assembly is variably positionable along the longitudinal axis of said orifice mount to selectively control the minimum distance from said orifice to a tissue target.

24. The high velocity liquid jet dental instrument of claim 15, wherein said guide tube includes a linear tube having an open distal end for passing said jet beam to a tissue target.

25. The high velocity liquid jet dental instrument of claim 24, wherein said guide tube includes an interior surface having a helical conformation to apply a turbulent, swirling rifling influence to said jet beam.

26. The high velocity liquid jet dental instrument of claim 15, wherein said guide tube includes a linear tube having a distal end closed by an oblique end wall, said end wall intercepting said jet beam and deflecting said jet beam to form a high velocity divergent spray.

27. The high velocity liquid jet dental instrument of claim 26, said guide tube including an output port in a sidewall portion thereof, said output port disposed in alignment with said high velocity divergent spray.

28. A high velocity liquid jet dental instrument, including:

reservoir means for supplying liquid to said jet;

pressure intensifier means for receiving liquid from said reservoir means and generating a high pressure liquid output;

a dental handpiece;

first valve means for controlling the flow of said high pressure liquid output to said handpiece;

jet orifice means in said handpiece for receiving said high pressure liquid output and forming a high velocity, narrow jet beam; and, bubble detector means interposed between said reservoir means and said pressure intensifier means for detecting interruption in liquid supply and stopping said pressure intensifier means.

* * * * *